United States Patent

Trick

[11] Patent Number: 5,101,813
[45] Date of Patent: Apr. 7, 1992

[54] PENILE ERECTILE SYSTEM AND METHOD FOR STERILIZATION

[75] Inventor: Robert E. Trick, Racine, Wis.

[73] Assignee: Medical Engineering Corporation, Racine, Wis.

[21] Appl. No.: 460,448

[22] Filed: Jan. 3, 1990

Related U.S. Application Data

[63] Continuation-in-part of Ser. No. 887,069, Jul. 17, 1986, Pat. No. 4,726,360, and a continuation-in-part of Ser. No. 145,629, Jan. 19, 1988, abandoned.

[51] Int. Cl.$^5$ ............................................. A61F 2/26
[52] U.S. Cl. .................................................... 600/40
[58] Field of Search ........................................ 128/79

[56] References Cited

U.S. PATENT DOCUMENTS

| | | | |
|---|---|---|---|
| 4,235,227 | 11/1980 | Yamanaka | 128/79 |
| 4,559,931 | 12/1985 | Fischell | 128/79 |
| 4,597,765 | 7/1986 | Klatt | 128/79 X |
| 4,604,994 | 8/1986 | Sealfon | 128/79 |
| 4,718,410 | 1/1988 | Hakky | 128/79 |

Primary Examiner—Robert P. Swiatek
Attorney, Agent, or Firm—Quarles & Brady

[57] ABSTRACT

A sterile, fully assembled, multi-component, penile erectile system which is to be surgically implanted in man for the treatment of erectile impotence includes at least one elongated, flexible cylindrical member with a pressure chamber for implanting into the pendulous penis; a pressure bulb to be implanted in the scrotal sac; tubing integrally connecting the pressure chamber and the bulb to form a closed system; and, a system for adding or subtracting fluid from the system. The tubing is reinforced so that it will not collapse under suction or kink when bent. In one embodiment the pressure bulb is a multi-stroke pump and in another embodiment there is a receptacle for storing any tubing in excess of that required to extend between two or more components in a given patient. A method of sterilizing and packaging the system so that it can be provided to a surgeon assembled, filled and sterile is also described.

4 Claims, 5 Drawing Sheets

PENILE ERECTILE SYSTEM AND METHOD FOR STERILIZATION

RELATED APPLICATON

This application is a continuation-in-part of my earlier patent applications Ser. No. 887,069 filed July 17, 1986, now U.S. Pat. No. 4,726,360, and Ser. No. 145,629 filed Jan. 19, 1988, and now abandoned.

FIELD OF THE INVENTION

The present invention relates to medical devices. More particularly, it relates to a penile erectile system for curing erectile impotence and a method of filling and sterilizing the systems.

BACKGROUND OF THE INVENTION

In some instances of erectile impotence in which the patient does not respond to more conventional therapy, the surgical implanting of a penile erectile system may be the only practical means of remedying the impotency.

In the past, several types of medical devices have been employed. The first type was a pair of silicone rods of suitable stiffness each of which was surgically implanted into a corpus cavernosum of the penis. One disadvantage of the use of the rods was that their stiffness made it difficult to implant rods of sufficient diameter and as a result the penis in the erectile state did not have a normal erectile girth. In addition, the penis was always rigid.

Another type of medical device which has been employed was an inflatable penile erectile system. The most widely used inflatable penile erectile system is that shown in U.S. Buuck Pat. No. 3,954,102. It includes two fairly long inflatable distensible tubes that are surgically implanted in the corpora cavernosa of the penis. Each of the two tubes is connected by tubing to valves, a pressure bulb and a reservoir for pressurizing fluid. The distensible tubes are collapsible and they can be easily implanted; when they are inflated they increase in diameter so that the girth of the penis is similar to that of a normal erection. The pressure bulb and reservoir are implanted elsewhere in the patient's body.

A simpler type of inflatable penile erectile system is that of the Uson U.S. Pat. No. 4,009,711. It consists of two cylindrical implants each connected by tubing to its own relatively large pressurizing bulb. Each implant includes a non-distensible stem portion made of a relatively stiff material to support the implant and an integral collapsible balloon-like distensible portion which is implanted into the corpora of the pendulous penis. The distensible portions are inflated by squeezing the bulbs which are implanted in the scrotum. The distensible portions increase in diameter when inflated so that the girth of the penis is similar to that of a normal erection.

The penile erectile system disclosed in Finney et al. U.S. Pat. No. 4,201,202 combines features of both the rod implant and the inflatable systems. It comprises a pair of implants each having a rod with a sleeve attached about a portion of the rod to form an inflatable chamber. It also includes a pressure bulb for inflating the chambers, a valve and tubing connecting the pressure bulb to the chambers. The implants are implanted in the corpora and the pressure bulb is implanted in the scrotum. When the inflatable chamber is pressurized the girth of the penis resembles that of a normal erection. The sleeve which forms the inflatable chamber may be made non-distensible so that the girth of the implant and the penis can be kept within predetermined levels.

All the described inflatable systems have an advantage over the rod implants in that they provide more natural appearing erections. However, these inflatable systems have a number of components and they are not commercially available in a preassembled, prefilled and pre-sterilized form.

A surgeon desiring to use one of the described systems is supplied with a kit containing the various components, such as cylinders and pressure bulbs, with lengths of tubing attached to each of the components. The surgeon fills each of the components separately with sterile pressurizing liquid through the attached tubing, shortens the tubing to the correct length, if necessary, and then connects the components into a closed system using tube connectors as shown in the Fogarty U.S. Pat. No. 4,537,183. The components of the kit and the pressurizing fluid can be supplied sterile by the manufacturer of the system, but because of the surgeon's need to fill and assemble the system the sterility of the final closed system cannot be assured.

Recently, several new inflatable, penile erectile systems have become commercially available. They basically consist of a pair of cylinders which can be implanted completely in the penis. Each of the cylinders which is about the size of a rod implant contains its own internal pump, reservoir and pressure chamber. These systems have an important advantage over the multi-component systems in that they can be supplied assembled, filled and sterilized by the manufacturer. However, these systems are more expensive than the multi-component inflatable systems with a scrotal pump. In addition, they do not provide as natural an erection because the girth of the penis is not increased.

It would be desirable to have an improved, inflatable penile erectile system which can be supplied to the surgeon completely assembled and sterilized.

SUMMARY OF THE INVENTION

It is the general object of the present invention to disclose a relatively inexpensive, inflatable penile erectile system which can be supplied to the surgeon completely assembled and sterilized by the manufacturer.

It is a further object to disclose such a system in which the penile girth can be variably adjusted.

It is also an object to disclose a completely assembled, sterilized, inflatable erectile system which includes a cylinder for implanting in the penis, a pressure pump for implanting elsewhere in the body, integral tubing connecting the cylinder to the pump and means for storing any excess length of tubing.

It is also an object to disclose methods of filling and sterilizing such a system.

It is still further an object to disclose a novel multistroke pump for use in an inflatable penile erectile system.

The present invention basically comprises a sterile, completely assembled penile erectile system consisting of at least one elongated, flexible, cylindrical member which is to be implanted in the pendulous penis, a pressure bulb which is to be implanted in the scrotum and integral tubing which connects the bulb to a pressure chamber in the cylindrical member to form a closed system. The pressure bulb is either a single stroke bulb which sucks fluid from the pressure chamber or a unique multi-stroke pump which is capable of higher pressure with less actuating force than a single stroke bulb.

In an especially preferred embodiment, the system also includes improved means for adding or subtracting fluid from the system; tubing which will not kink or collapse; and means for storing any excess length of the integral tubing not needed in the operation.

In another embodiment, the cylindrical member includes a second, girth increasing, outer chamber positioned radially about the pressure chamber, a passage connecting the outer and pressure chambers, and valve means for controlling the flow of liquid from the pressure chamber to the outer chamber so that the penile girth can be adjusted.

The novel method of the present invention comprises assembling the system, filling it with a working amount of fluid, sterilizing the system, placing the filled, assembled and sterilized system in a vapor impervious pouch, evacuating and sealing the pouch and then sterilizing the evacuated, sealed pouch and its contents with steam and pressure.

DESCRIPTION OF THE PREFERRED EMBODIMENT

As seen in FIGS. 1 to 7 of the drawings, the penile erectile system 10 comprises a pair of a elongated cylindrical members 11, 11', a pressure bulb assembly 12 and tubing 13, 13' connecting the bulb 12 to the members 11, 11'. The cylindrical members 11, 11' are identical, therefore, only the cylindrical member 11 will be described.

Figure 1:
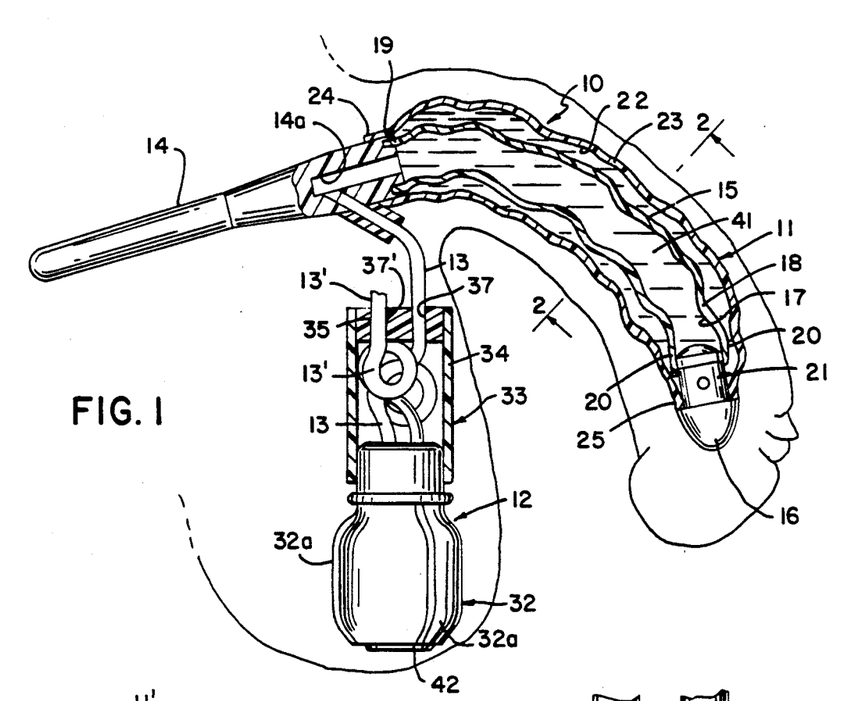
FIG. 1 is a partial sectional view of the penile erectile system of the present invention surgically implanted in a male with the pressure chamber depressurized.
Figure 4:
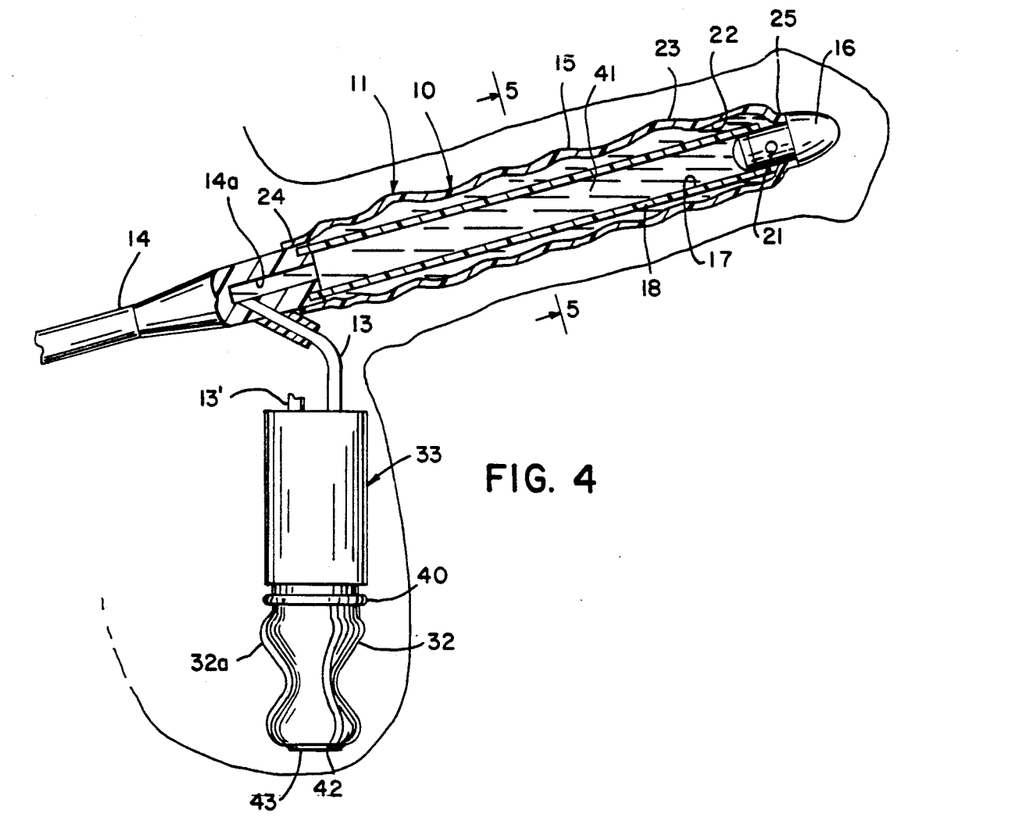
FIG. 4 is a view similar to FIG. 1, except the pressure chamber is fully pressurized.
Figures 6, 7:
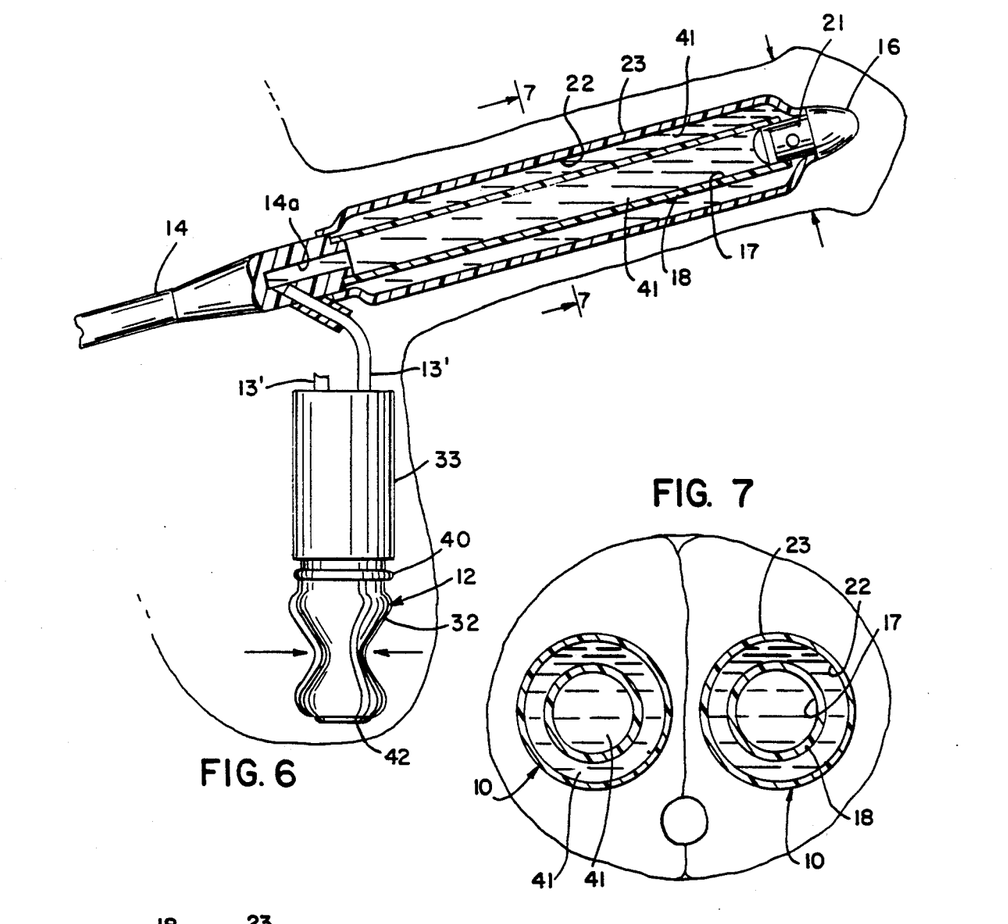
FIG. 6 is a view similar to FIG. 1 but showing that liquid has been transferred to the outer chamber to increase girth.
FIG. 7 is a view taken along line 7—7 in FIG. 6.

As seen best in FIGS. 1, 4 and 6, the cylindrical member 11 is provided with a short, trimmable proximal portion or stem 14 of relatively stiff material which is implanted in the root end of a corpus cavernosum to support and anchor the implant, and a longer distal portion 15 of a softer, more flexible material which is implanted into the portion of corpus cavernosum in the pendulous penis. The distal portion 15 is provided with a tip 16 which is paraboloidal in shape to conform to the inner shape of the end of the corpus cavernosum.

Positioned within the distal portion 15 is a pressure chamber 17 which is formed by an inner sleeve 18 of non-distensible material, preferably silicone coated fabric which 18 is sealed at one end 19 to the inner end of the stem 14 and at the other end 20 to a valve block 21 in a fluid-tight manner. The seals between the ends 19 and 20 of the sleeve 18 and the stem 14 and valve block 21 are preferably made with a suitable silicone adhesive.

Figures 2, 3:
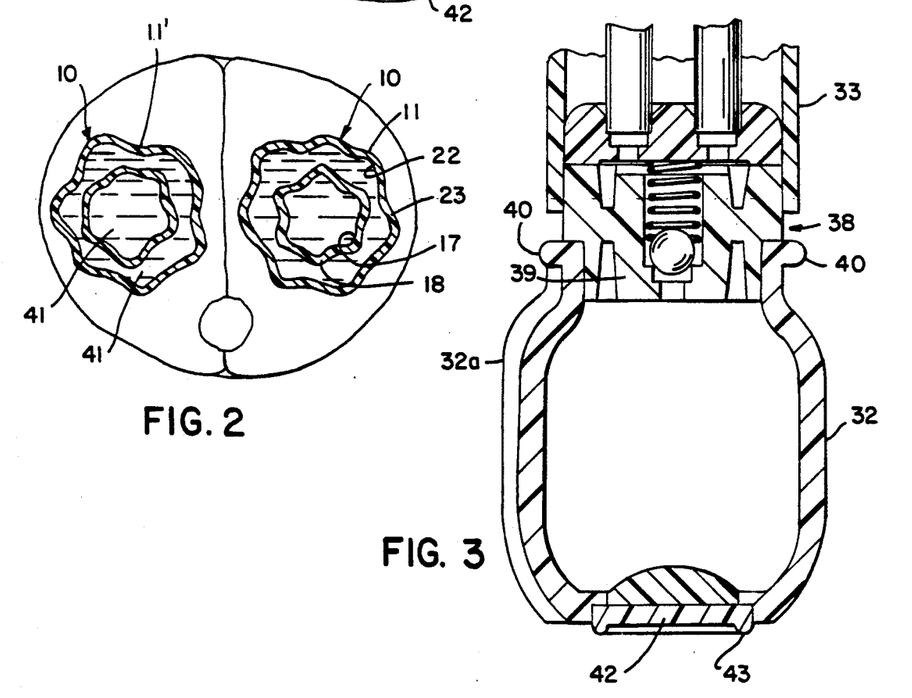
FIG. 2 is a cross sectional view taken along the lines 2—2 in FIG. 1.
FIG. 3 is an enlarged sectional view of the pressure bulb of FIG. 1.
Figure 5:
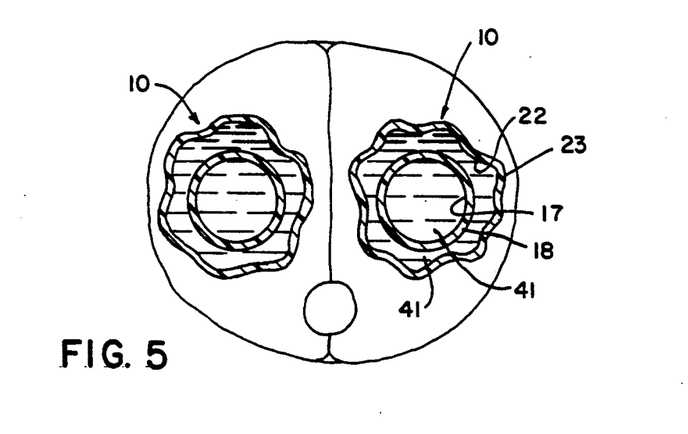
FIG. 5 is a view taken along line 5—5 in FIG. 4.

As seen in FIGS. 2, 5 and 7 there is a second concentric chamber 22 positioned radially outward from the pressure chamber 17. Referring back to FIGS. 1, 4 and 6 it can be seen that the chamber 22 is formed by a second sleeve 23 of material which is sealed at its ends 24, 25 to the stem 14 and valve block 21 in a manner similar to sleeve 18. The sleeve 23 may be of either distensible or non-distensible material.

Figure 8:
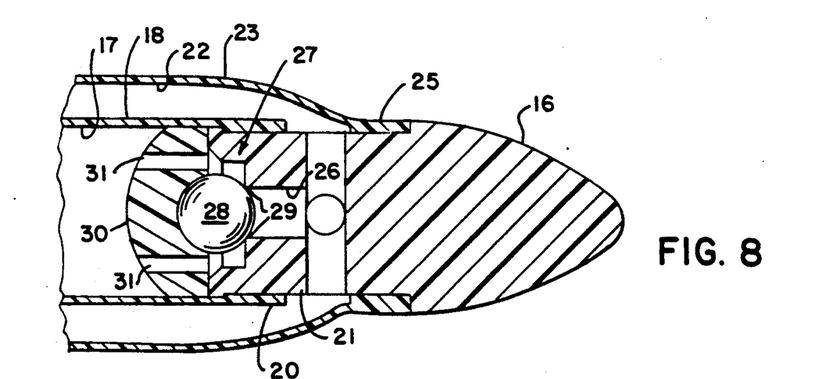
FIG. 8 is an enlarged sectional view of the tip of the implant of FIG. 6.

As seen in FIG. 8, the chambers 17 and 22 are connected by a passage 26 which extends through the valve block 21. Liquid flow through the passage 26 is controlled by a valve means generally referred to as 27 which is located within the valve block 21 and includes a ball 28, a ball seat 29 and a ball retaining member 30. The ball 28, which is normally kept seated on the seat 29 by the retainer 30, can be moved from its normal position closing the-passage 26 to a position in which the passage 26 is open to flow by deforming the block 21. When the ball 28 is off its seat 29 liquid can flow from the pressure chamber 17 through the passages 31 in the retainer 30 and the passage 26 into chamber 22. The valve block 21 is made of a readily deformable plastic material so that the valve means 27 can be readily opened manually from the outside by deforming the valve block 21 to unseat the ball 28.

Referring again to FIGS. 1, 4 and 6, it can be seen that communication between the pressure chamber 17 and the pressure bulb assembly 12 is provided by a passage 14a, which passes through the solid stem 14, and a length of the tubing 13.

Figure 10:
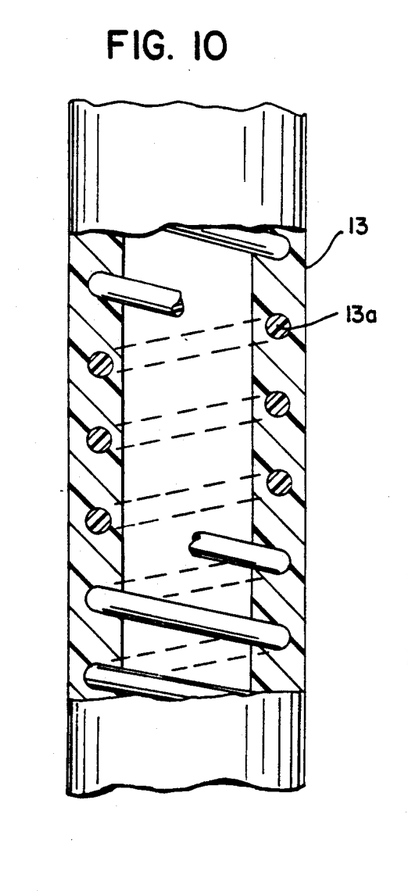
FIG. 10 is an enlarged sectional view showing the preferred tubing of the system of FIG. 1.

The tubing 13 is preferably reinforced with a reinforcing monofilament 13a, seen only in FIG. 10. The monofilament 13a, which is preferably of polyester, prevents the tubing from kinking or collapsing when it is bent or subjected to suction created by the bulb 12.

As seen in FIGS. 1 and 3, one end of the tubing 13 is operatively connected to the passage 14a and the other end is operatively connected to a pressure bulb 32. In the preferred embodiment seen in FIGS. 1 and 3, the pressure bulb assembly 12 includes an excess tubing storage means 33. The tubing length requirements can vary with the patient's anatomy and the surgical technique employed. Therefore, the system is provided with the longest length of integral tubing required. The excess length of tubing over that actually required for a specific operation can be discomforting to the patient and asthetically distracting; it is stored until needed in the storage means 33.

The storage means 33 comprises a receptacle 34 for safely storing any excess tubing 13 and a closure 35 closing the open mouth 36 of the receptacle 34. The closure 35 is interrupted by a pair of passageways 37, 37' through which any excess tubing 13, 13' stored in the receptacle 34 can be withdrawn as needed.

As seen best in FIG. 3, the pressure bulb 32, which is to be implanted in the scrotal sac of a patient, is provided with a number of ribs 32a, preferably six, which both reinforce the bulb 32 and provide traction making it easier for the user to squeeze the bulb from outside the scrotal sac.

Still referring to FIG. 3, it can be seen that the pressure bulb assembly 12 also includes a valve 38 for controlling the flow of pressurizing fluid between the pressure bulb 32 and the pressure chamber 17. The valve 38 is normally closed, but it can be opened by either manually squeezing the pressure bulb 32 or by deforming the housing 39 of the valve 38. The housing 39 is provided with an enlarged external flange 40 which makes it easier for the user to find the housing 39 in the scrotal sac and insures that user will squeeze the housing 39 in proper location to open the valve 38 when it is desired to deflate the pressure chamber 17.

The valve 38 is of the type which opens when the pressure bulb 32 is squeezed and closes when the bulb 32 is released. After the reinforced bulb 32 has been squeezed and the valve 38 is closed, the bulb 32 remains collapsed as seen in FIGS. 4 and 6 until the valve 38 is once again opened by the user deforming the housing 39. At that time the reinforced, resilient bulb 32 returns to its original volume and shape (seen in FIG. 1) and in the process creates a suction of about 15 cm/H$_2$O to about 20 cm/H$_2$O which actively sucks the pressurizing fluid out of the pressure chamber 17, thus causing it to empty sufficiently so that the penis will assume a normal, flaccid state.

Referring back to FIG. 1, it can be seen that when the chamber 17 of the implant is not pressurized the soft, relatively flexible distal portion 15 of the member 11 permits the penis to assume a substantially normal, flaccid position. In the flaccid position, as seen in FIG. 2, the chamber 17 is not completely filled with the pressurizing fluid 41.

Referring now to FIGS. 4 and 5, it can be seen that when the chamber 17 is pressurized the soft, flexible distal portion 15 of the member 11 is supported by the pressurized chamber 17 and the penis assumes a substantially normal erectile form. In the erectile form, seen in FIGS. 4 and 5, the pressure chamber 17 is completely filled with the fluid 41 and the distensible outer chamber 22 is partially filled.

Referring now to FIGS. 6 and 7 the use of the implant 10 to increase penile girth will be described. If the first valve means 27 is opened by deforming the valve block 21 and the pressure bulb 32 is simultaneously squeezed to open the second valve 38 the pressurizing liquid 41 will flow via the tubing 13 and the passage 14a into the inner cylinder 17 and via passage 26 into the outer chamber 22 causing it to fill and increase penile girth. When the valve block 21 is no longer deformed the valve 27 closes and the liquid 41 which has been transferred from the pressure chamber 17 is retained in the chamber 22. If desired, the transferred liquid 41 in chamber 22 can be moved back to chamber 17 by deforming the valve block 21 to open the valve 27 while squeezing the distal portion 15 of the implant.

Figure 9:
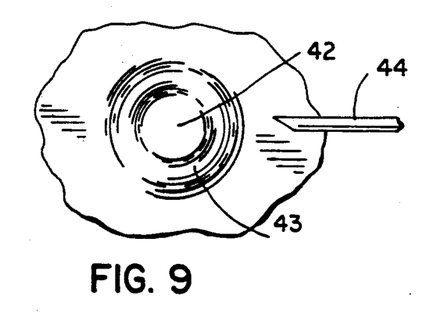
FIG. 9 is an enlarged bottom view of the pressure bulb of FIG. 3 as seen through the scrotal skin showing a cannula poised to pierce the self sealing valve.

A one-way valve 42, which is seen best in FIG. 3 permits fluid to be added or removed from the closed system. The preferred valve 42 is a septum made of prestressed fabric encapsulated in silicone elastomer. As seen best in FIGS. 3 and 9 the valve 42 is surrounded by a raised rib 43. Referring to FIG. 9, it can be seen that when the raised rib 43 is pressed against the inner surface of the scrotal skin it can be seen through the skin. Thus, the surgeon is provided with a clear target for the proper placement of a needle 44 to add or subtract fluid from the bulb 32 and system via the valve 42.

Figure 12:
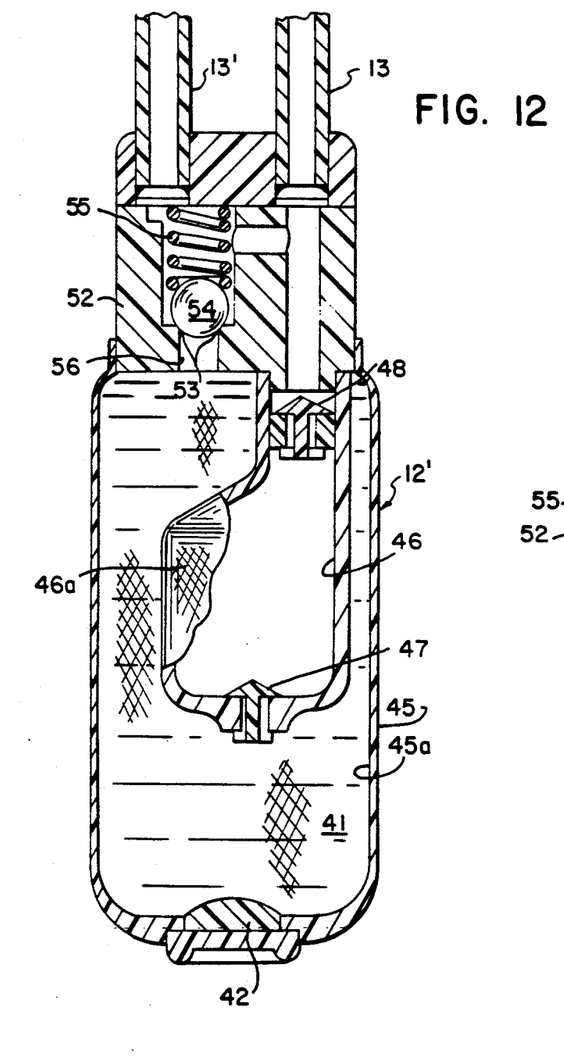
FIG. 12 is a sectional view of the novel multi-stroke pump of the present invention.
Figure 13:
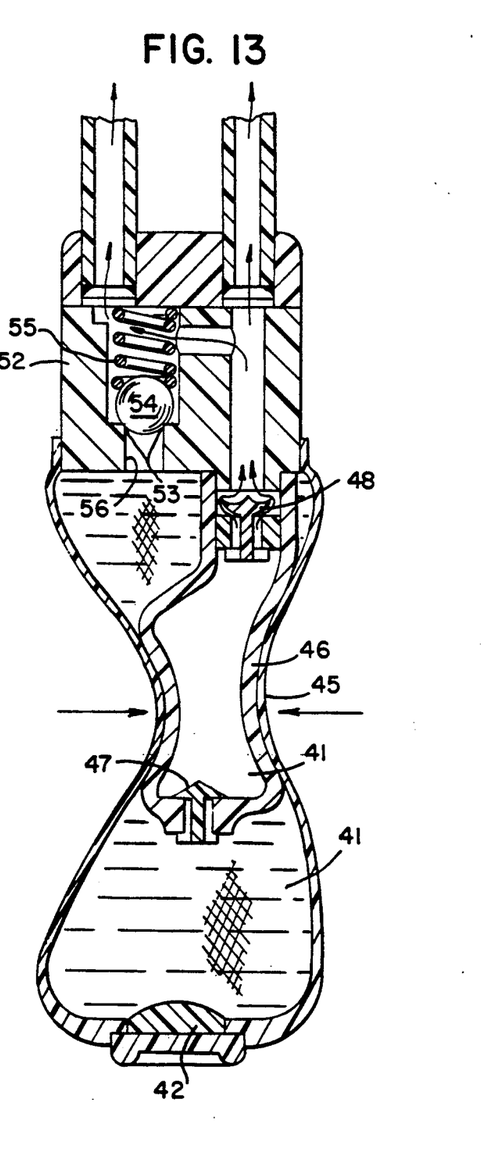
FIG. 13 is a view similar to FIG. 12 showing the pump being squeezed.

In FIGS. 12 and 13 a novel multi-stroke pump assembly 12' is shown which is capable of high pressure and requires less actuating force than larger displacement simple one stroke bulb pumps.

The multi-stroke pump assembly 12' can be used in place of the pump bulb assembly 12 in the penile erectile system shown in FIG. 1. Although not shown in the drawings, the pump assembly 12 can be provided with the tubing storage means 33, if desired.

The multi-stroke pump assembly 12' consists of an outer reservoir chamber 45 and an inner pumping chamber 46. When force is extended on the pump assembly, as shown in FIG. 13, pressurizing fluid 41 in the reservoir 45 is forced through the inlet check valve 47 and outlet check valve 48 of the pumping chamber 46 and through the passageways 49, 50 and 51 to the supply tubing 13, 13' to the pressure chambers. As additional force is applied contact will be made between the inner wall 45a of the reservoir 45 and the outer wall surface 46a of the pumping chamber. Therefore, the inner wall 45a and the outer wall 46a are preferably textured to prevent the slipping of these surfaces while pumping. The force is released after the pump assembly 12' is fully stroked whereupon the pumping chamber 46 resumes its original shape and pressurizing fluid 41 fills the pumping chamber 46 through inlet valve 47. The pump assembly 12' is repeatedly stroked until the pressure chambers are fully pressurized. The outlet valve 48 prevents the back flowing of fluid 41 from the pressure chambers.

When it is desired to depressurize the pressure chambers, force is exerted on the housing 52 to distort the seat 53 for the ball 54 and to allow pressurized fluid 41 to flow over the ball 54 into the reservoir 45. When the distorting force is released on the housing 52 the spring 55 will direct the ball 54 back into sealing engagement with the seat 53 and the passage 56 will be closed.

The multi-stroke pump assembly can be provided with a one way valve 42 on the type previously described so that fluid can be added to or removed from the assembled system.

The described multi-stroke pump also can be used in penile systems, such as that shown in the Bucck et al. U.S. Pat. No. 3,954,102, or in an incontinence device to replace both a pump and a separate reservoir, as well as, potentially troublesome suction tubing.

As previously described, the prior art penile erectile systems which consisted of cylinders, tubing and pressure bulbs, had cylinders and bulbs which were each provided with connected lengths of tubing. The tubing was used by the surgeon to fill the cylinder or bulb with fluid, the tubing was trimmed to the proper length, if needed, and the ends of the tubing joined together with connectors and sutures to close the system. In contrast, the erectile system of the present invention can be fully assembled into a closed system by the manufacturer by integrally joining the opposite ends of the kinkless tubing 13 to the cylindrical members 11, 11' and bulb assembly 12 or 12', respectively.

The length of the tubing 13 which is selected to connect the cylindrical member 11 and bulb assembly 12 is the longest length that might be required in a normal operation. As seen in FIG. 1, the tubing 13 in excess of that required in a specific operation to reach from the bulb 32 in the scrotum to the cylinder 11 in the penis is stored in the excess tube storage means 33. As a practical matter, the system 10 as supplied by the manufacturer will have the shortest length of tubing required to extend between the cylinder 11 and bulb 32 in a patient extending out of the storage means 33. Thereafter, if additional tubing 13 is required by the surgeon for the operation it will be withdrawn from the storage means 33 as needed.

The assembled system is filled by the manufacturer with a working amount of pressurizing liquid 41 via the valve 42 so that the chamber 17 is full, but not rigid, and the tubing and pressure bulb are full. If desired a small amount of the liquid can also be introduced into the outer girth, increasing chamber 22 of the preferred embodiment to insure that its walls will not stick together as a result of the sterilization procedure.

Figure 11:
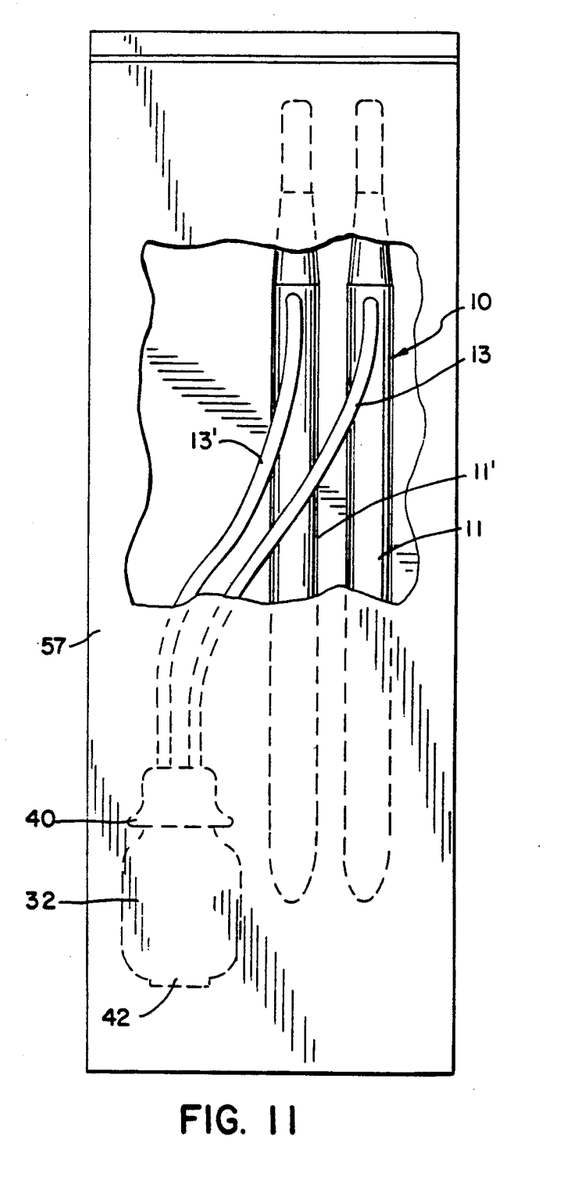
FIG. 11 is a view, partly in section, of a sterile package containing a filled, assembled implant of FIG. 1.

In the preferred sterilization method, the assembled system 10 is first placed in a moisture impervious pouch containing an effective amount of water (e.g. 20 ml), and sanitized at 250° F. in autoclave for 15 minutes at a steam gauge pressure of 30–38 psi. The system 10 is then filled and placed in a moisture impervious, dry pouch 57 (see in FIG. 11) and the pouch 57 and its contents placed in a conventional vacuum sealer (not shown). The vacuum sealer draws a vacuum and then automatically seals the pouch 57. The sealed pouch 57 and the system 10 are then sterilized in an autoclave at 250° F. for 180 minutes at a steam gauge pressure of 30–38 psi.

Once the sterilization is complete the sterile packaged penile erectile system 10 can be stored until used by a surgeon. The only adjustment that may have to be made by the surgeon prior to implanting the system 10 is to remove any gases originally present in the liquid 41 that have left the liquid during sterilization and collected in the system. The removal of gases is readily accomplished without destroying the sterility of the system by aspirating the gas from the bulb 32 with a sterile needle and syringe via the valve 42 in a sterile field.

The preferred method of implantation of the system 10 is through a single incision. After the appropriate incision is made, the corpora cavernosa are dilated distally and proximally to accept the cylindrical number 11, 11'. The approximate anatomical measurements are made to insure that the proximal portions 14, 14 will be positioned at the base of the penis below the pelvic bone. Cylindrical members having appropriately sized distal portions are selected and the distal portions inserted into the corpora cavernosa of the penis. The proximal stems 14, 14 can be trimmed to the appropriate length.

As seen in the drawings the proximal stem 14 of the penile implant 10 at all times is anchored in the root end of the corpus cavernosum, and the paraboloidal tip 16 is positioned in the glans end of the corpus cavernosum. As a result, the implant 10 is positioned correctly in the corpus cavernosum of the penis and the likelihood of displacement is minimized.

In the preferred embodiment of the invention the sleeve 18 is preferably made of a silicone elastomer coated woven or knit fabric which provides to a limited pre-determined expansion to allow the penis to become longer and to contain the pressure so that the tunica albuginea will not distend. Alternatively, the sleeve 18 also can be made of a material which does not distend either axially or longitudinally.

The diameter of the sleeve 18 is sufficient to form a functional pressure chamber 17. The use of a sleeve material which does not distend or distends only to a limited extent makes it possible to raise the fluid pressure in the chamber 17 to the desired high level with only a minimum of pressurizing fluid. The sleeve 23 may be made of unreinforced silicone rubber or any functionally equivalent or superior material.

The term "non-distensible" as used herein is intended to cover chambers which are functionally non-distensible or of limited distensibility under conditions of use normally encountered with the erectile system.

In the preferred embodiment, all the parts and components of the prosthesis are made of medical application silicone rubber which is non-reactive, non-toxic and well tolerated by the adjacent organic tissues. Silicone rubber is preferred because it is quite resistant to wear and tear and remains functional for long periods of time. However, other suitable materials may be employed, if desired.

It will be readily apparent to those skilled in the art to which this invention relates that a variety of changes and modifications might be made without departing from the spirit and scope of the invention.

For example, if desired, the sleeves 18 and 23 may take the initial shape of curved tubular members as opposed to the straight cylinders described and shown in the drawings. The forming of curved tubular sleeves in approximately the shape that the sleeves assume when the implant is in the depressurized state minimizes the likelihood of folds forming which can be encapsulated by scar tissue. However, in order to permit the curved tubular sleeve to assume the shape of a cylinder upon pressurization, it may be necessary to have selected longitudinal threads of the woven or knit fabric of the sleeve crimped to permit a limited longitudinal extension.

From the foregoing, it will be apparent that the description has been for purposes of illustration and is not intended to be limiting. For example, although an implant with an anchoring stem has been described it will be appreciated that other anchoring means can be used, if desired. Furthermore, although the preferred embodiment uses a common pressure bulb for two separate cylinders, other embodiments could employ one pressure bulb for each cylinder. Therefore, it is intended that the invention not be limited except by the claims which follow.

I claim:

1. A method of filling and sterilizing a penile erectile system comprising at least one cylindrical member for implanting in the pendulous penis, pressurizing means for implanting in the scrotum, tubing integrally connecting the pressurizing means to at least one cylindrical member to form a closed system and means for adding or subtracting fluid from said system, said method comprising:
   (a) integrally connecting at least one cylindrical member, tubing and pressurizing means to form a closed system;
   (b) placing the assembled system in a first vapor impermeable container;
   (c) sterilizing the system;
   (d) removing the sterilized system from the first container;
   (e) introducing a working level of liquid into said system via the means for adding or subtracting fluid;
   (f) placing the previously sterilized system containing a working level of liquid in a second vapor impermeable container;
   (g) evacuating and sealing said second container; and
   (h) sterilizing said sealed second container and its contents with steam and pressure.

2. A penile erectile system comprising at least one elongated, flexible cylindrical member for implanting in the corpus cavernosum of the penis of a patient, said at least one member including a pressure chamber; pressurizing means for delivering pressurizing fluid to said pressure chamber; tubing connecting the pressure chamber and the pressurizing means into a closed system; and, means for storing tubing in excess of that required.

3. A penile erectile system comprising at least one elongated, flexible cylindrical member for implanting in the corpus cavernosum of the penis of a patient, said at least one member including a pressure chamber; pressurizing means for delivering pressurizing fluid to said pressure chamber; integral tubing connecting the pressure chamber and the pressurizing means into a closed system; and, means for storing the integral tubing which is in excess of that required to extend from the pressure chamber to the pressurizing means.

4. In a penile erectile system comprising at least one elongated, flexible, cylindrical member for implanting in the corpus cavernosum of the penis of a patient, said at least one member including a pressure chamber, pressurizing means for delivering pressurizing fluid to said pressure chamber, and tubing connecting the pressure chamber and pressurizing means into a closed system; the improvement which comprises an improved pressurizing means which consists of a pressure bulb implanted in the scrotal sac, said pressure bulb having an inner chamber and an outer chamber, said pressure bulb being so constructed that when the pressure bulb is squeezed fluid is initially transferred under low pressure and at a high flow rate to the pressure chamber from the outer chamber, and when the outer chamber is substantially emptied and the squeezing continues, fluid is transferred under high pressure from the inner chamber to the pressure chamber.

* * * * *